United States Patent
Kumagai et al.

(10) Patent No.: US 10,028,673 B2
(45) Date of Patent: Jul. 24, 2018

(54) MEASURING DEVICE

(71) Applicant: Tanita Corporation, Tokyo (JP)

(72) Inventors: Masahiko Kumagai, Daisen (JP); Takashi Sasaki, Daisen (JP); Toshiaki Shindo, Daisen (JP)

(73) Assignee: TANITA CORPORATION, Tokyo (JP)

( * ) Notice: Subject to any disclaimer, the term of this patent is extended or adjusted under 35 U.S.C. 154(b) by 82 days.

(21) Appl. No.: 14/711,629

(22) Filed: May 13, 2015

(65) Prior Publication Data
US 2015/0342498 A1 Dec. 3, 2015

(30) Foreign Application Priority Data
May 30, 2014 (JP) .................. 2014-112355

(51) Int. Cl.
A61B 5/053 (2006.01)
A61B 5/00 (2006.01)
G01G 19/50 (2006.01)

(52) U.S. Cl.
CPC .......... A61B 5/0537 (2013.01); A61B 5/6843 (2013.01); G01G 19/50 (2013.01); A61B 2560/0468 (2013.01)

(58) Field of Classification Search
None
See application file for complete search history.

(56) References Cited

U.S. PATENT DOCUMENTS

| 5,886,302 | A | * | 3/1999 | Germanton | ............ G01G 19/44 174/135 |
| 2007/0103451 | A1 | | 5/2007 | Heimann et al. | |
| 2009/0085188 | A1 | | 4/2009 | Yamada | |
| 2009/0264790 | A1 | * | 10/2009 | Ashida | .................. A61B 5/0537 600/547 |
| 2012/0296231 | A1 | * | 11/2012 | Osoegawa | ............ A61B 5/0537 600/547 |

FOREIGN PATENT DOCUMENTS

EP 1 786 107 B1 5/2007
JP 08-181257 A 7/1996
(Continued)

OTHER PUBLICATIONS

JP2003059567A Machine Translation.*
Extended European Search Report dated Jul. 16, 2015, Application No. 15168118.6, 8 pages.

Primary Examiner — Devin Henson
Assistant Examiner — Benjamin Melhus
(74) Attorney, Agent, or Firm — Foley & Lardner LLP

(57) ABSTRACT

A measuring device comprises: a first housing having at least one measuring electrode; a second housing connected to the first housing and housing a substrate which has at least one terminal and includes a circuit that conducts a measurement process; and at least one connecting member disposed between the first housing and the second housing. The at least one connecting member is formed of a unitary member. One end of the at least one connecting member is connected to the at least one terminal, while the other end of the at least one connecting member is in contact with the at least one measuring electrode due to an elastic force of the at least one connecting member itself.

11 Claims, 6 Drawing Sheets

(56) References Cited

FOREIGN PATENT DOCUMENTS

| | | | |
|---|---|---|---|
| JP | 2003-059567 A | | 2/2003 |
| JP | 2003059567 A | * | 2/2003 |
| JP | 2010-012037 A | | 1/2010 |
| JP | 2010-315988 U | | 5/2010 |
| JP | 2011-185689 A | | 9/2011 |
| JP | 2014-027186 A | | 2/2014 |

* cited by examiner

MEASURING DEVICE

CROSS-REFERENCE TO RELATED APPLICATION

This application is based on and claims the benefit of priority of the prior Japanese Patent Application No. 2014-112355, filed on May 30, 2014, the entire contents of which are incorporated herein by reference.

BACKGROUND OF THE INVENTION

1. Field of the Invention

The present invention relates to a measuring device.

2. Description of the Related Art

In a measuring device such as a body composition meter, measuring electrodes are placed in contact with the hands and/or feet to measure the body weight or bioelectrical impedance of a human body. Information such as bioelectrical impedance obtained through the measuring electrodes is sent as electrical signals to, for example, an operation circuit provided on a substrate, is subjected to the operation of the operation circuit, and is then sent to a user as information on the body composition such as body fat rate.

An example of a known measuring device of this kind is a weighing device disclosed in Japanese Laid-open Patent Publication 2011-185689. This weighing device has: a weighing pan; a damper having a built-in piezoelectric element and disposed on a lower surface of the weighing pan; and an auxiliary power supply unit electrically connected via a lead to the piezoelectric element. When an object to be measured is placed on the weighing pan, a load is applied to the piezoelectric element built in the damper to supply a power to the auxiliary power unit via the lead.

Since the piezoelectric element and the auxiliary power supply unit are connected to each other by the lead in the weighing device disclosed in Japanese Laid-open Patent Publication 2011-185689, however, it has the following problems. When the weighing device is assembled, a process of soldering the lead to the piezoelectric element is required. More specifically, it is necessary to place the weighing pan after the piezoelectric element and the auxiliary power supply unit are connected by the lead in advance, and, therefore, there seems to be a limitation in the assembly process. In addition, the use of soldering and a lead may cause failure or defect of electrical connection, because the solder joint may degrade and the lead may break due to long-term use. The present invention has been made to solve the above problems.

BRIEF SUMMARY OF THE INVENTION

An object of the present invention is to provide a measuring device which can be easily assembled and can be stably used for a long time.

According to one aspect of the present invention, this object is achieved by a measuring device comprising: a first housing having at least one measuring electrode; a second housing connected to the first housing and housing a substrate which has at least one terminal and is used for making measurements; and at least one connecting member disposed between the first housing and the second housing, wherein the at least one connecting member is formed of a unitary member, and wherein one end of the at least one connecting member is connected to the at least one terminal, while the other end of the at least connecting member is in contact with the at least one measuring electrode due to an elastic force of the at least one connecting member itself.

While the novel features of the present invention are set forth in the appended claims, the present invention will be better understood from the following detailed description taken in conjunction with the drawings.

BRIEF DESCRIPTION OF THE DRAWINGS

The present invention will be described hereinafter with reference to the annexed drawing. It is to be noted that the drawing is shown for the purpose of illustrating the technical concepts of the present invention or embodiments thereof, wherein.

DETAILED DESCRIPTION OF THE INVENTION

Exemplary embodiments of the present invention will be described hereinafter with reference to the drawings. It is to be understood that the embodiments described herein are not intended as limiting, or encompassing the entire scope of, the present invention.

Figure 1:
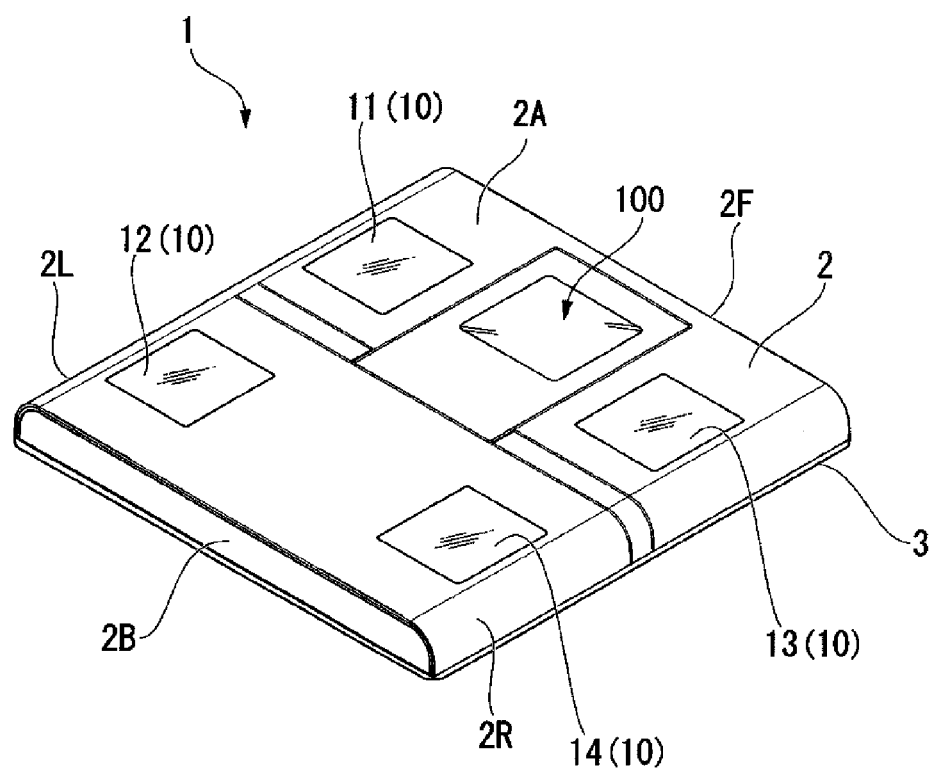
FIG. 1 is a schematic perspective view showing an appearance of a measuring device according to an embodiment of the present invention.
Figure 2:
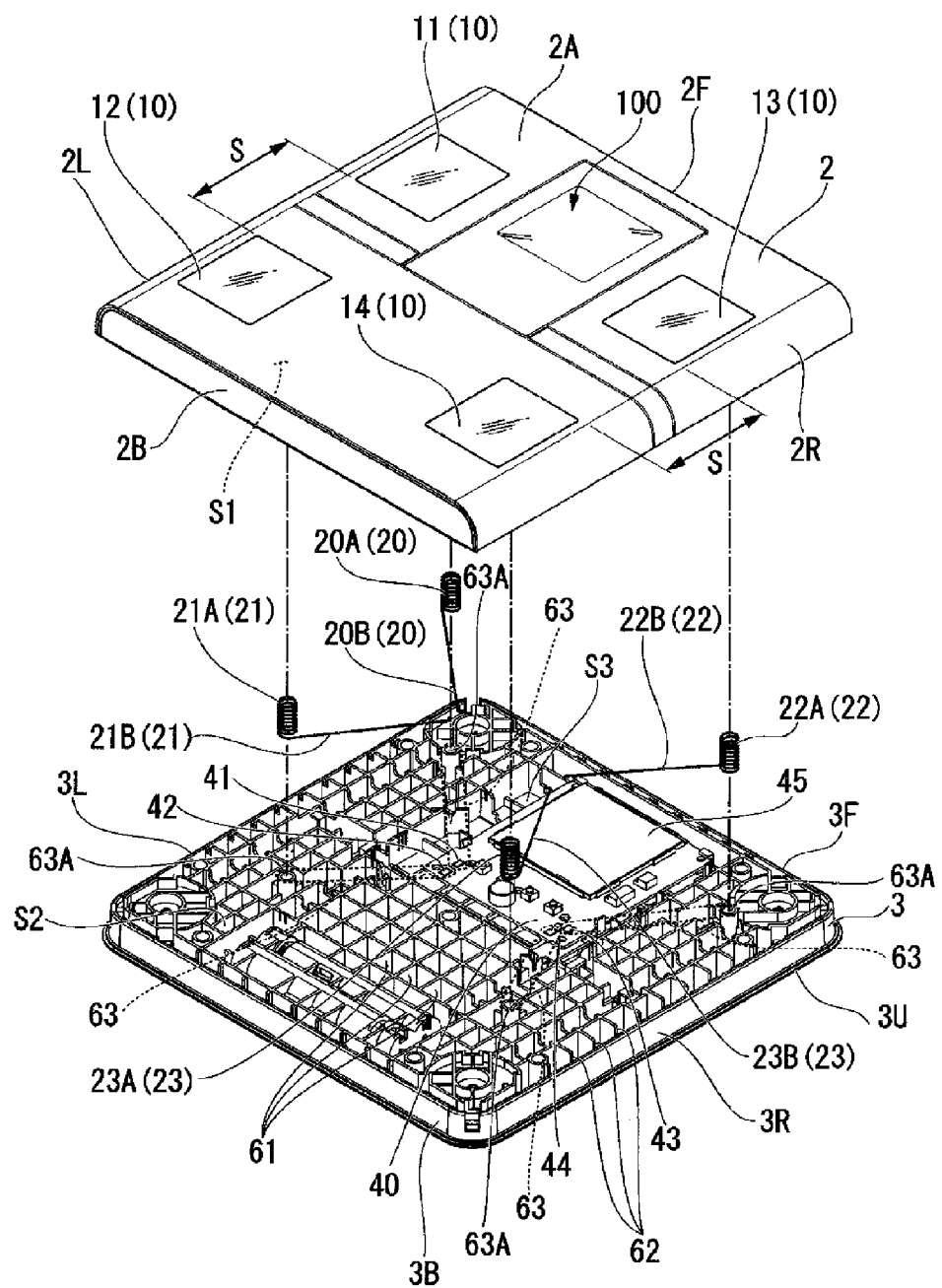
FIG. 2 is a schematic exploded perspective view showing the structure of the measuring device.

A measuring device 1 according to an exemplary embodiment of the present invention will be described with reference to FIG. 1 to FIG. 8. FIG. 1 is a schematic perspective view showing an appearance of the measuring device 1, while FIG. 2 is a schematic exploded perspective view showing the structure of the measuring device 1. As shown in FIG. 1 and FIG. 2, the measuring device 1 comprises: a first housing 2 having a plurality of measuring electrodes 10 on an upper surface thereof; a second housing 3 connected to the first housing 2 and housing a substrate 40 therein; and a plurality of connecting members 20, 21, 22, and 23 disposed between the first housing 2 and the second housing 3.

The first housing 2 comprises: a top plate 2A formed in a square shape in top view; and a left side wall 2L, a right side wall 2R, a front wall 2F and a back wall 2B which respectively extend downward from the top plate 2A. Note that in the following description, the direction extending from the front wall 2F to the back wall 2B (i.e. the direction in which a user commonly steps on and off when using it) will be referred to as front-back direction. More specifically, the side where the front wall 2F is positioned will be expressed as e.g. front or front side, while the side where the back wall 2B is positioned will be expressed as e.g. back or back side.

The top plate 2A and each of the left side wall 2L and the right side wall 2R form a connecting portion therebetween having a curved shape. More specifically, the connecting portion between the top plate 2A and the left side wall 2L is gradually curved from the top plate 2A toward the left side wall 2L, and similarly the connecting portion between the top plate 2A and the right side wall 2R is gradually curved from the top plate 2A toward the right side wall 2R. The top plate 2A and each of the front wall 2F and the back wall 2B intersect substantially perpendicular to each other. Each of the front wall 2F and the back wall 2B has two upper corner portions, each of which is formed to have a curved shape when viewed in the front-back direction. In other words, the two upper corner portions are formed in an arc corresponding to the curved shape formed between the top plate 2A and each of the side walls 2L and 2R. On the other hand, each of the front wall 2F and the back wall 2B has two lower corner portions, each of which is formed to make a substantially right angle when viewed in the front-back direction.

Here, the area under the top plate 2A that is surrounded by the front wall 2F, the back wall 2B, the left side wall 2L and the right side wall 2R is referred to as space S1. The space S1 opens downward. Further, the front wall 2F, the back wall 2B, the left side wall 2L and the right side wall 2R are set to have the same vertical dimension as each other. The first housing 2 having the above structure is integrally formed, for example, of a resin material. Furthermore, the top plate 2A has the plurality of measuring electrodes 10 formed thereon which are placed in contact with a human body to be measured for various measurements. Each of the measuring electrodes 10 comprises an electrode member having a square shape in top view and formed in a thin plate shape. Four measuring electrodes 10 are provided near the four corners of the top plate 2A, respectively.

More specifically, the measuring electrodes 10 comprise: a first measuring electrode 11 and a second measuring electrode 12 arranged in the front-back direction along one side of the top plate 2A close to the left side wall 2L; and a third measuring electrode 13 and a fourth measuring electrode 14 arranged in the front-back direction along one side of the top plate 2A close to the right side wall 2R. The first measuring electrode 11 and the third measuring electrode 13 are electrodes for supplying current. In other words, a current supplied by a current supply device (not shown) flows between the first measuring electrode 11 and the third measuring electrode 13, and flows into the body of the user.

On the other hand, the second measuring electrode 12 and the fourth measuring electrode 14 are electrodes used for making measurements. When current flows between the first measuring electrode 11 and the third measuring electrode 13 as described above, a potential difference is generated between the second measuring electrode 12 and the fourth electrode 14. This potential difference is detected by the second measuring electrode 12 and the fourth measuring electrode 14. The first measuring electrode 11 and the third measuring electrode 13 are spaced from the second measuring electrode 12 and the fourth measuring electrode 14, respectively, by a predetermined distance. More specifically, the distance S between one side of the first measuring electrode 11 (the third measuring electrode 13) and one side of the second measuring electrode 12 (the fourth measuring electrode 14), facing the one side of the first measuring electrode 11 (the third measuring electrode 13), is, for example, about 70 mm.

Each of the measuring electrodes 10 has an upper surface formed in a smooth flat surface and exposed outward from above the top plate 2A. Further, each measuring electrode 10 has a lower surface formed in a smooth flat surface and exposed toward the above-described space S1 from below the top plate 2A. In other words, each measuring electrode 10 is arranged to penetrate through the top plate 2A in the thickness direction. Note that each measuring electrode 10 is fixed to the top plate 2A by a fixing member (not shown) so as to prevent the measuring electrode 10 from dropping off Although each measuring electrode 10 described above is arranged to penetrate through the top plate 2A in the thickness direction, it is also possible to form a recess in an upper surface of the top plate 2A, and to form, in a portion of the recess, a through-hole extending through a lower surface of the top plate 2A, so as to place the measuring electrode 10 in the recess.

The upper surface of each measuring electrode 10 and the upper surface of the top plate 2A are formed so as to be smoothly connected to each other. This makes it possible to make measurements without causing a raised portion of the measuring electrode 10 to put unnecessary pressure on a human body when the measuring electrode 10 is in contact with the human body, and also makes it possible to ensure aesthetic appearance of products. A display window 100 is provided in an area of the top plate 2A between the first electrode 11 and the third electrode 13. At least a part of the display window 100 is formed of a transparent resin, glass or the like so as to inform measurement results displayed on a display unit 45, which is provided on a substrate 40 described later, to the outside through the display window 100.

The second housing 3 is a box-shaped member having a base and is connected to the above-described first housing 2 in the vertical direction. The second housing 3 comprises: a bottom plate 3U formed in a substantially square shape in top view; and a second housing front wall 3F, a second housing back wall 3B, a second housing left side wall 3L and a second housing right side wall 3R which extend upward respectively from the bottom plate 3U and substantially perpendicular to the bottom plate 3U. The second housing front wall 3F, the second housing back wall 3B, the second housing left side wall 3L and the second housing right side wall 3R are set to have substantially the same vertical dimension as that of the front wall 2F, the back wall 2B, the left side wall 2L and the right side wall 2R of the first housing 2, respectively.

Here, the area over the bottom plate 3U of the second case 3 and surrounded by the second housing front wall 3F, the second housing back wall 3B, the second housing left side wall 3L and the second housing right side wall 3R is referred to as space S2. The space S2 is divided into a plurality of sections by a plurality of longitudinal ribs 61 extending in the front-back direction and a plurality of lateral ribs 62 extending in a direction perpendicular to the longitudinal ribs 61. The longitudinal ribs 61 and the lateral ribs 62 are plate-like members extending upward respectively from the bottom plate 3U. When the user steps on the measuring device 1, the longitudinal ribs 61 and the lateral ribs 62 can withstand the load (weight of the user), since the space S2 is divided by the plurality of longitudinal ribs 61 and lateral ribs 62. Thus, the space S2 is not broken by the weight of the user, allowing the measuring device 1 to maintain its shape. Note that a front area of the space S2 is not provided with either the longitudinal ribs 61 or the lateral ribs 62, and is used as a substrate housing section S3. A substrate 40 described later is housed in the substrate housing section S3, and, therefore, the shape and dimensions of the substrate housing section S3 are determined by the shape and dimensions of the substrate 40. In the present embodiment, the substrate housing section S3 is substantially square-shaped in top view.

The substrate 40 comprises: a circuit (not shown) for conducting a measurement process by using signals obtained from the measuring electrodes 10 described above; and a display unit 45 for displaying output results of the circuit. On the substrate 40, terminals 41, 42, 43 and 44 electrically connected to the circuit via printed wiring are provided. Measured values obtained from the measuring electrodes 10 are input to the terminals 41, 42, 43 and 44 via the connecting members 20, 21, 22 and 23, respectively. The connecting members 20, 21, 22, and 23 are housed in the space S2 of the second housing 3. Although the longitudinal ribs 61 and the lateral ribs 62 are provided in the space S2 of the second housing 3 as described above, the longitudinal ribs 61 and the lateral ribs 62 are notched to form housing grooves 63 in the areas of the space S2 where the connecting members 20, 21, 22 and 23 are housed, respectively. The housing grooves 63 are linear grooves extending in the same plane along the direction from the terminals 41, 42, 43 and 44 on the substrate 40 toward the first measuring electrode 11, the second measuring electrode 12, the third measuring electrode 13 and the fourth measuring electrode 14, respectively.

More specifically, the housing groove 63 from the terminal 41 toward the first measuring electrode 11 extends substantially diagonally left forward from the substrate 40. The housing groove 63 from the terminal 42 toward the second measuring electrode 12 extends substantially diagonally left backward from the substrate 40. The housing groove 63 from the terminal 43 toward the third measuring electrode 13 extends substantially diagonally right forward from the substrate 40. Further, the housing groove 63 from the terminal 44 toward the fourth measuring electrode 14 extends substantially diagonally right backward from the substrate 40.

A conductive member holding member 63A is provided at an end of each housing groove 63, which is located opposite to where the substrate 40 is located. Each conductive member holding member 63A is a substantially cylindrical-shaped boss portion which extends upward from the bottom plate 3U in the space S2. The conductive member holding members 63A engage with and hold conductive members 20A, 21A, 22A and 23A, respectively, which will be described later. Note that, as described above, the space S2 is an area over the bottom plate 3U of the second case 3 and surrounded by the second housing front wall 3F, the second housing back wall 3B, the second housing left side wall 3L and the second housing right side wall 3R.

The connecting members 20, 21, 22 and 23 have the same shape and the same dimension as each other, and therefore, the connecting members 20, 21, 22 and 23 have the same dimension (length) as each other from one end to the other end of each thereof. Thus, one of the connecting members, i.e., connecting member 20, will be described in detail below as a representative. The connecting member 20 comprises: a conductive member 20A which is a coil spring, as an elastic member, wound around an axis extending in a vertical direction (i.e. in the direction in which the first housing 2 is connected to the second housing 3); and a linear lead member 20B which extends from a lower end of the conductive member 20A in a direction perpendicular to the vertical direction and is integrally formed with the conductive member 20A. The conductive member 20A (hence the connecting member 20) is elastically deformable in the vertical direction (i.e. in the direction in which the first housing is connected to the second housing), and is formed of a metal material having good conductivity.

Figure 3:
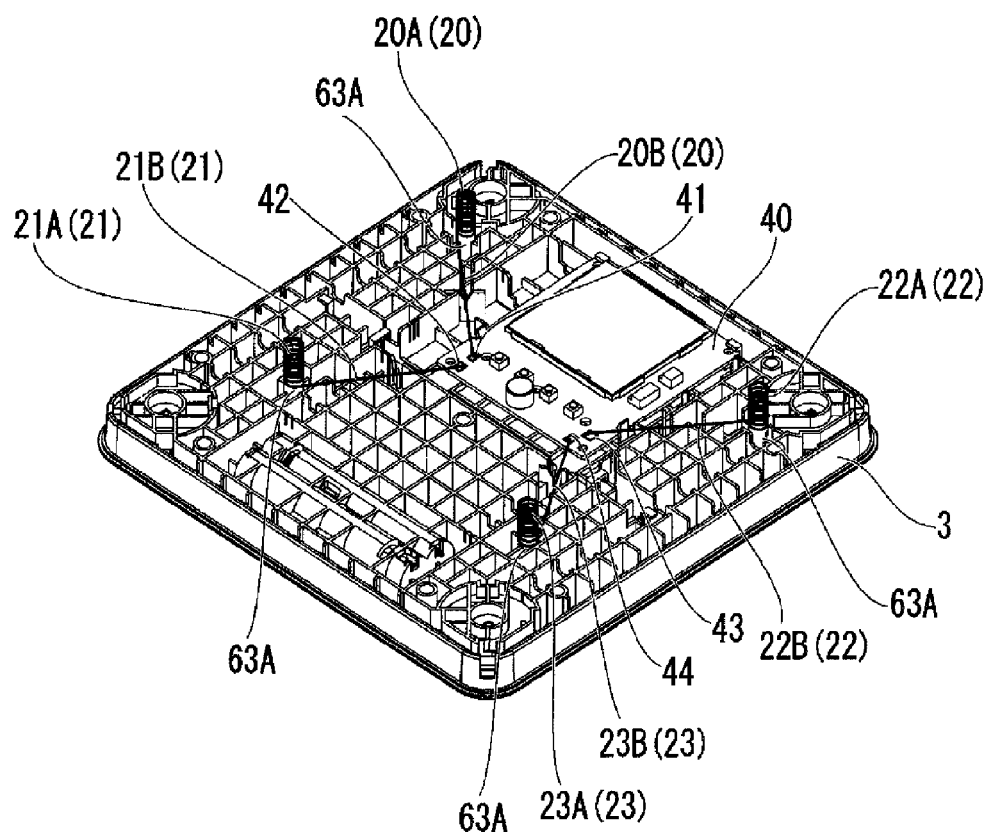
FIG. 3 is a schematic perspective view showing a state in which a second housing and connecting members in the measuring device are assembled together.

In the following explanation, a process of assembling the measuring device 1 will be described. First, the second housing 3 to constitute a lower part of the measuring device 1 is prepared. Subsequently, the substrate 40 and the connecting members 20, 21, 22 and 23 are arranged in the second housing 3. The substrate 40 is housed in the substrate housing section S3 described above, and is fixed therein by screws or the like, for example, so as to prevent the substrate 40 from falling off. The connecting members 20, 21, 22 and 23 are housed in the four housing grooves 63, respectively, which are areas between the first housing 2 and the second housing 3. More specifically, the lead members 20B, 21B, 22B, and 23B of the connecting members 20, 21, 22 and 23 are housed in the housing grooves 63, respectively, which are formed in the space S2 of the second housing 3. Further, the conductive members 20A, 21A, 22A and 23A are held by the corresponding conductive member holding members 63A, respectively. This is shown in FIG. 3, which is a schematic perspective view showing a state in which the second housing 3 and the connecting members 20, 21, 22, and 23 in the measuring device 1 according to the exemplary embodiment of the present invention are assembled together. Next, the ends of the lead members 20B, 21B, 22B and 23B, which are located opposite to where the conductive members 20A, 21A, 22A and 23A are provided, are connected by soldering or the like, for example, to the terminals 41, 42, 43 and 44, respectively, which are provided on the substrate 40.

More specifically, the conductive members 20A, 21A, 22A and 23A are fitted to the corresponding conductive member holding members 63A, respectively, from above so as to be held thereby. In other words, the dimensions in the radial directions of the conductive member holding members 63A are set to be substantially the same as (i.e., completely the same as, a little larger than or a little smaller than) the inner diameters of the coil springs of the conductive members 20A, 21A, 22A and 23A, respectively. Note that the dimension in the radial direction of each conductive member holding member 63A can be designed to decrease from a lower end to an upper end of the conductive member holding member 63A. Further note that it is also possible to house the substrate 40 and the connecting members 20, 21, 22 and 23 in the substrate housing section S3 and the housing grooves 63, respectively, after the connecting members 20, 21, 22 and 23 are connected to the terminals 41, 42, 43 and 44 of the substrate 40, respectively, in advance. However, in terms of workability and quality, it is more desirable to connect the connecting members 20, 21, 22 and 23 to the terminals 41, 42, 43, and 44 of the substrate 40, respectively, after the substrate 40 is housed in the substrate housing section S3.

Figure 4:
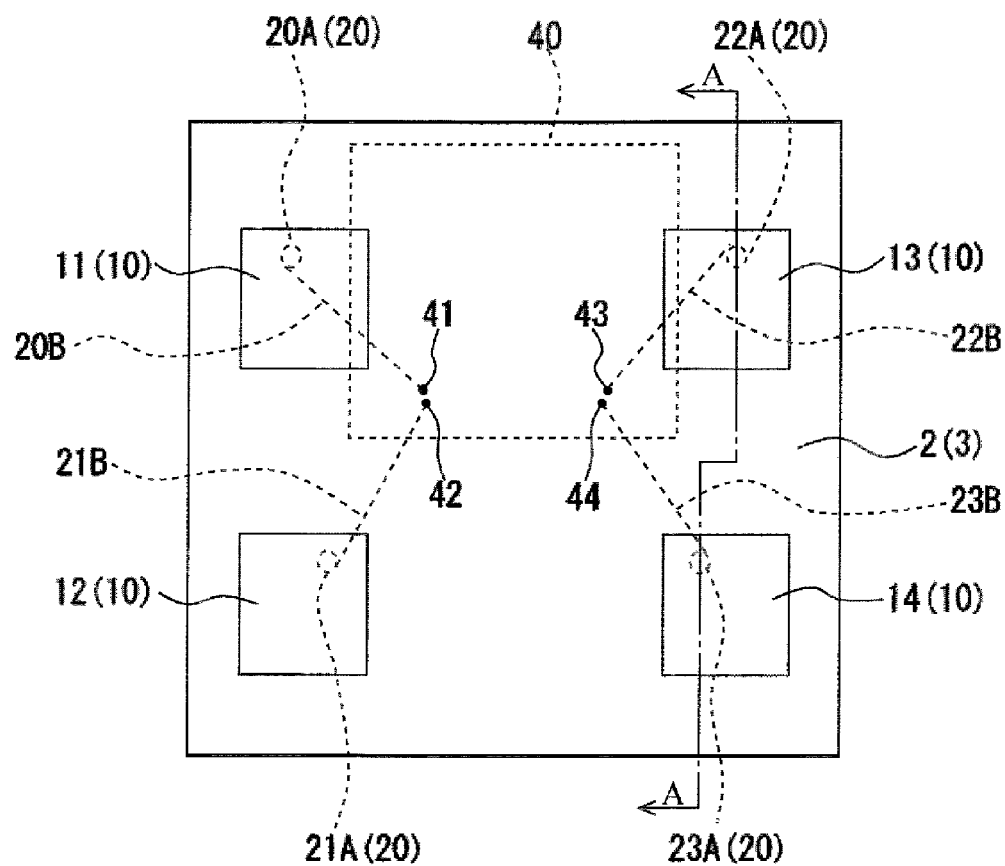
FIG. 4 is a schematic top plan view of the measuring device.

Next, the first housing 2 is connected to the second housing 3. Note that the measuring electrodes 10 described above are assumed to be fixed to the first housing 2 in advance of the connection. The first housing 2 and the second housing 3 are connected together by connecting members (not shown). An example of such connecting member can be a combination of an elastically deformable locking claw and a locking hook engaged with the locking claw. It is also possible to provide one of the first housing 2 and the second housing 3 with screws and provide the other with screw holes to connect the first housing 2 and the second housing 3. Accordingly, the assembly of the measuring device 1 is completed. FIG. 4 is a schematic top plan view of the measuring device 1 thus assembled. As shown in FIG. 4, the assembled measuring device 1 is structured such that, when viewed from the direction in which the first housing 2 is connected to the second housing 3, i.e. from the vertical direction, the positions where the conductive members 20A, 21A, 22A and 23A are held have overlaps with the first measuring electrode 11, the second measuring electrode 12, the third measuring electrode 13 and the fourth measuring electrode 14, respectively.

Figure 5:
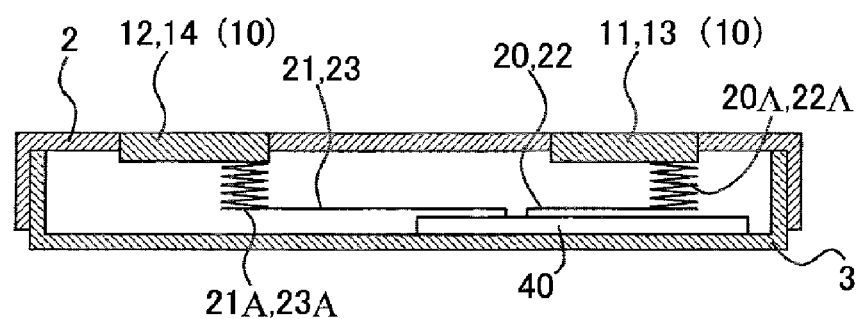
FIG. 5 is a schematic cross-sectional view of the measuring device taken along line A-A of FIG. 4.

This will be described in more detail with reference to FIG. 5, which is a schematic cross-sectional view of the measuring device 1 taken along line A-A of FIG. 4. Note that the longitudinal ribs 61 and the lateral ribs 62 are abbreviated in FIG. 5. As shown in FIG. 5, in the assembled measuring device 1, the upper ends of the conductive members 20A, 21A, 22A and 23A are in contact with the lower surfaces of the first measuring electrode 11, the second measuring electrode 12, the third measuring electrode 13 and the fourth measuring electrode 14 of the first housing 2, respectively. In addition, each of the conductive members 20A, 21A, 22A and 23A is in a state of being compressed in the vertical direction. In other words, the conductive members 20A, 21A, 22A and 23A are in contact with the first measuring electrode 11, the second measuring electrode 12, the third measuring electrode 13 and the fourth measuring electrode 14 due to the elastic restoring force of themselves. Thus, the first measuring electrode 11, the second measuring electrode 12, the third measuring electrode 13 and the fourth measuring electrode 14 are electrically connected to the substrate 40 through the connecting members 20, 21, 22, and 23, respectively.

In the measuring device 1 described above, the conductive members 20A, 21A, 22A and 23A are integrally formed with the lead members 20B, 21B, 22B and 23B, respectively. In other words, the connecting members 20, 21, 22 and 23 comprise linear lead members 20B, 21B, 22B, and 23B integrally formed with the conductive members 20A, 21A, 22A, and 23A (each corresponding to claimed "coil spring"), respectively. Thus, when assembling the measuring device 1, the conductive members 20A, 21A, 22A and 23A can be connected to the lead members 20B, 21B, 22B and 23B, respectively, without soldering. For example, if leads separate from the conductive members 20A, 21A, 22A and 23A are used as the lead members 20B, 21B, 22B and 23B described above, these leads need to be electrically connected to the conductive members 20A, 21A, 22A and 23A, respectively, by a process such as soldering. However, such a process is not required in the present embodiment, so that the assembly process can be simplified.

Furthermore, in the measuring device 1 according to the present embodiment, each of the conductive members 20A, 21A, 22A and 23A is formed of an elastic member, which is a coil spring. According to this structure, it is possible that the first measuring electrode 11, the second measuring electrode 12, the third measuring electrode 13 and the fourth measuring electrode 14 provided on the first housing 2 are in contact with the conductive members 20A, 21A, 22A and 23A, respectively, only by connecting the first housing 2 to the second housing 3 from above, and that the state of contact can be maintained substantially permanently as long as the elastic restoring force of the conductive members 20A, 21A, 22A and 23A remains. Thus, the measuring device 1 can be stably used for a long time.

As described above, according to the measuring device 1 of the present exemplary embodiment, the connecting members 20, 21, 22 and 23 are elastically deformable in the direction in which the first housing 2 is connected to the second housing 3. Thus, only by connecting the first housing 2 and the second housing 3 to each other, the connecting members 20, 21, 22, and 23 can be in contact with and electrically connected to the measuring electrodes 11, 12, 13, and 14 provided on the first housing 2. Further, the measuring device 1 of the present embodiment is designed so that the connecting members 20, 21, 22, and 23 each formed of a unitary member are in contact with the first measuring electrode 11, the second measuring electrode 12, the third measuring electrode 13 and the fourth measuring electrode 14, respectively, due to the elastic force of the connecting members 20, 21, 22, and 23 themselves. Thus, as compared with the case in which soldering is used to connect the measuring electrodes 11, 12, 13, and 14 to the connecting members 20, 21, 22, and 23, it is possible to reduce working man-hours and easily assemble the measuring device 1, and to use the measuring device 1 stably for a long time, because, by not soldering, the joints between the measuring electrodes 11, 12, 13, and 14 and the connecting members 20, 21, 22, and 23 can be prevented from degrading.

Further, the measuring device 1 described above is structured such that, when viewed from the direction in which the first housing 2 is connected to the second housing 3, i.e. from the vertical direction, the positions where the conductive members 20A, 21A, 22A and 23A are held (i.e. the connecting members 20, 21, 22, and 23 are held) in the second housing 3 have overlaps with the positions of the first measuring electrode 11, the second measuring electrode 12, the third measuring electrode 13 and the fourth measuring electrode 14, respectively. According to this structure, the positions where the conductive members 20A, 21A, 22A and 23A are arranged can be freely changed depending on the dimensions of the measuring electrodes 11, 12, 13 and 14, respectively, making it possible to increase the degree of freedom in designing the measuring device 1.

Further, the measuring device 1 has a structure that the connecting members 20, 21, 22, and 23 have coil springs (conductive members 20A, 21A, 22A, and 23A) each wound around an axis extending in the direction in which the first housing 2 is connected to the second housing 3. According to this structure, due to the elastic restoring force of the coil springs (conductive members 20A, 21A, 22A, and 23A), the ends of the connecting members 20, 21, 22, and 23 (at which ends the conductive members 20A, 21A, 22A, and 23A are provided) are in contact with and electrically connected to the first measuring electrode 11, the second measuring electrode 12, the third measuring electrode 13 and the fourth measuring electrode 14, respectively, which are provided on the first housing 2.

In addition, in the measuring device 1, the distances (lengths) from the conductive members 20A, 21A, 22A, and 23A to the terminals 41, 42, 43, and 44 on the substrate 40, respectively, are designed to be the same as each other.

Figure 6:
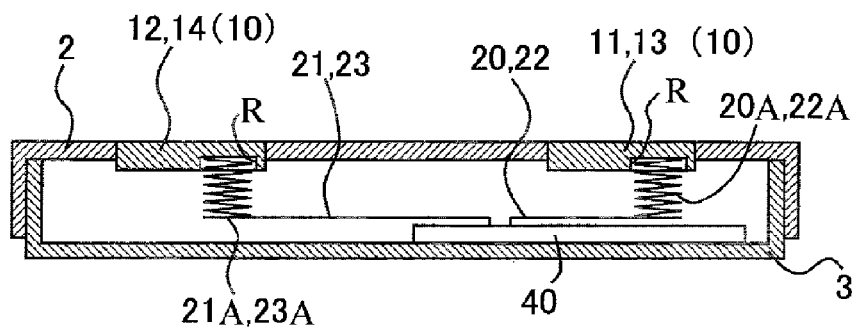
FIG. 6 is a schematic cross-sectional view of a modified example of the measuring device taken along line A-A of FIG. 4.

While an exemplary embodiment of the present invention has been described above in detail with reference to the drawings, the present invention is not limited to the embodiment described above, and is to cover all modifications and variations without departing from the spirit of the present invention. For example, in the embodiment described above, each measuring electrode 10 has a lower surface formed in a smooth flat surface. Instead, however, recesses R can be formed each in the lower surface of each electrode 10 as shown in FIG. 6, which is a schematic cross-sectional view of a modified example of the measuring device 1 taken along line A-A of FIG. 4. Each of the recesses R is formed to be recessed upward from the lower surface of the measuring electrode 10. In this case, the recesses R are formed to be slightly larger than the outer dimensions of the conductive members 20A, 21A, 22A and 23A, respectively.

In other words, the recesses R have shapes corresponding to shapes of the upper ends of the connecting members 20, 21, 22 and 23, respectively, which ends are in contact with the measuring electrodes, respectively, to allow the upper ends of the conductive members 20A, 21A, 22A and 23A to be housed in the recesses R, respectively. Since the measuring electrodes 10 are provided with the recesses R having shapes corresponding to the upper ends of the connecting members 20, 21, 22 and 23, the upper ends of the conductive members 20A, 21A, 22A and 23A can be fitted to the recesses R formed in the measuring electrodes 10, respectively. This makes it possible to reduce slippage between the conductive members 20A, 21A, 22A and 23A and the measuring electrodes 10. Note that the longitudinal ribs 61 and the lateral ribs 62 are abbreviated in FIG. 6.

Figure 7:
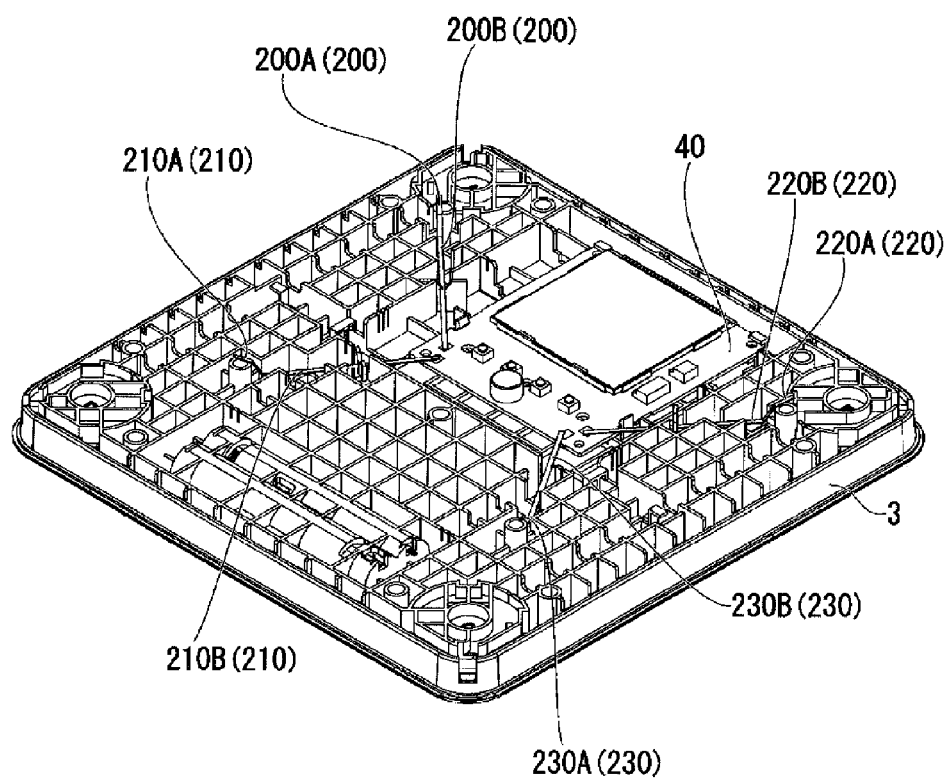
FIG. 7 is a schematic perspective view of a further modified example of the measuring device.
Figure 8:
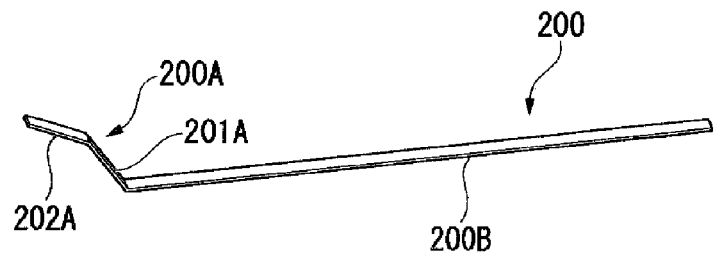
FIG. 8 is a schematic perspective view of a connecting member in the further modified example of the measuring device.

Further, in the embodiment described above, each of the conductive members 20A, 21A, 22A and 23A is formed of a coil spring. However, the conductive members 20A, 21A, 22A and 23A are not limited to coil springs as long as they are conductive and elastically deformable in the direction in which the first housing 2 is connected to the second housing 3 as described below with reference to FIG. 7 and FIG. 8. FIG. 7 is a schematic perspective view of a further modified example of the measuring device 1, while FIG. 8 is a schematic perspective view of a connecting member 200 in the further modified example of the measuring device 1. In FIG. 8, the connecting member 200 is shown as a representative of four connecting members 200, 210, 220 and 230 which correspond to the connecting members 20, 21, 22 and 23, respectively, described above.

As shown in FIG. 7 and FIG. 8, the conductive members 20A, 21A, 22A and 23A described above can be replaced by conductive members 200A, 210A, 220A, and 230A, each of which is a leaf spring elastically deformable in the direction in which the first housing 2 is connected to the second housing 3. Note that the connecting members 200, 210, 220 and 230 have the same shapes and dimensions as each other, and therefore, the connecting members 200, 210, 220, and 230 have the same dimension (length) as each other from one end to the other end of each thereof. Thus, one of the connecting members, i.e., connecting member 200, will be described in detail below as a representative.

The connecting member 200 comprises a lead member 200B formed in a strip shape, and a conductive member 200A which is a leaf spring integrally formed with the lead member 200B. More specifically, as shown in FIG. 8, the conductive member 200A has an inclined part 201A bent at a predetermined inclination angle relative to the lead member 200B, which extends linearly, so as to extend diagonally upward. The conductive member 200A further has a linear part 202A bent at a predetermined inclination angle relative to the inclined part 201A so as to extend diagonally upward at a slight inclination angle relative to the lead member 200B.

Here, when a load is applied to the linear part 202A from above, the linear part 202A functions as a leaf spring due to the elastic restoring force of the conductive member 200A, since the linear part 202A extends diagonally upward at a slight inclination angle relative to the lead member 200B. Further, the connecting member 200 has a width dimension set to be slightly smaller than the width dimension of the housing groove 63 described above. Thus, the connecting member 200 can be housed in the housing groove 63. According to this structure, similarly as in the embodiment described above, the connecting member 200 is formed of a unitary member having the conductive member 200A and the lead member 200B integral with the conductive member 200A. Thus, when assembling the measuring device 1, the conductive member 200A can be connected to the lead member 200B without soldering, so that the assembly process of the measuring device 1 can be simplified.

According to this structure, similarly as in the embodiment described above, only by connecting the first housing 2 to the second housing 3 from above, the ends of the connecting members 200, 210, 220, and 230 (conductive members 200A, 210A, 220A, and 230A) are in contact with and electrically connected to the first measuring electrode 11, the second measuring electrode 12, the third measuring electrode 13 and the fourth measuring electrode 14, respectively, which are provided on the first housing 2, due to the elastic restoring force of the conductive members 200A, 210A, 220A, and 230A which are leaf springs. Further, the state of contact can be maintained substantially permanently as long as the elastic restoring force of the conductive members 200A, 210A, 220A and 230A remains. Thus, the measuring device 1 can be stably used for a long time.

It is to be noted that the present invention is not limited to the above-described embodiments and modified examples, and various modifications are possible within the spirit and scope of the present invention. The present invention has been described above using exemplary embodiments, but such description should not be interpreted as limiting the present invention. Various modifications will become obvious, evident or apparent to those ordinarily skilled in the art, who have read the description. Accordingly, the appended claims should be interpreted to cover all modifications and alterations which fall within the spirit and scope of the present invention.

The invention claimed is:

1. A measuring device comprising:
    a first housing located on an upper side of the measuring device, the first housing comprising a measuring electrode;
    a second housing located on a lower side of the measuring device, the second housing being connected to the first housing and housing a substrate, the substrate comprising a terminal, and a circuit configured to conduct a measurement process; and
    a connecting member disposed between the first housing and the second housing,
    wherein the connecting member comprises a conductive member, and a linear lead member that extends from the conductive member,
    wherein an end of the linear lead member is connected to and in direct contact with the terminal, and an end of the conductive member is in contact with a respective measuring electrode due to an elastic force of the conductive member itself, and
    wherein the second housing comprises a housing groove that houses the linear lead member, wherein the housing groove extends in a direction perpendicular to a direction from the upper side to the lower side of the measuring device,
    wherein the housing groove extends from the terminal to the measuring electrode, and
    wherein the linear lead member extends in an entirely linear manner from the conductive member to the terminal within the housing groove.

2. The measuring device according to claim 1, wherein the conductive member is elastically deformable in the direction from the upper side to the lower side of the measuring device.

3. The measuring device according to claim 1,
wherein the measuring electrode comprises a recess having a shape corresponding to a shape of said end of a respective conductive member.

4. The measuring device according to claim 1,
wherein the second housing further comprises a conductive member holding member that engages with and holds the conductive member, and
wherein, when viewed from the direction from the upper side to the lower side of the measuring device, a position at which the conductive member is held by the conductive member holding member in the second housing has an overlap with a position of a respective measuring electrode.

5. The measuring device according to claim 1,
wherein the conductive member is a coil spring wound around an axis extending in the direction from the upper side to the lower side of the measuring device.

6. The measuring device according to claim 5,
wherein the linear lead member is integrally formed with the coil spring.

7. The measuring device according to claim 1,
wherein the conductive member is a leaf spring that is elastically deformable in the direction from the upper side to the lower side of the measuring device, which is a direction in which the first housing is connected to the second housing.

8. The measuring device according to claim 1,
wherein the measuring device comprises:
a plurality of connecting members, including the connecting member recited in claim 1,
a plurality of measuring electrodes, including the measuring electrode recited in claim 1, and
a plurality of terminals, including the terminal recited in claim 1, and
wherein the plurality of connecting members have the same dimension as each other from the end of the linear lead member to the end of the conductive member.

9. The measuring device according to claim 5,
wherein the second housing further comprises a boss portion that extends upward from a bottom plate of the second housing and that engages with and holds the coil spring.

10. The measuring device according to claim 9,
wherein, when viewed in the direction from the upper side to the lower side of the measuring device, a position at which the coil spring is held by the boss portion in the second housing has an overlap with a position of the measuring electrode.

11. The measuring device according to claim 9, wherein the boss portion is cylindrically-shaped.

* * * * *